USOO5750369A

United States Patent [19]
Lake et al.

[11] Patent Number: 5,750,369
[45] Date of Patent: May 12, 1998

[54] DNA ENCODING A PROSTAGLANDIN F2β RECEPTOR, A HOST CELL TRANSFORMED THEREWITH AND AN EXPRESSION PRODUCT THEREOF

[75] Inventors: Staffan Lake, Lidingö; Johan Stjernschantz, Uppsala, both of Sweden

[73] Assignee: Pharmacia & Upjohn Aktiebolag, Stockholm, Sweden

[21] Appl. No.: 416,756

[22] PCT Filed: Oct. 1, 1993

[86] PCT No.: PCT/SE93/00789

§ 371 Date: Apr. 13, 1995

§ 102(e) Date: Apr. 13, 1995

[87] PCT Pub. No.: WO94/07920

PCT Pub. Date: Apr. 14, 1994

[30] Foreign Application Priority Data

Oct. 2, 1992 [SE] Sweden .................................. 9202892

[51] Int. Cl.$^6$ .......................... C12N 15/09; C07K 14/705
[52] U.S. Cl. ................ 435/69.1; 435/252.3; 435/254.11; 435/320.1; 435/325; 536/23.5; 530/350; 530/395
[58] Field of Search ...................... 530/350, 395; 435/69.1, 240.1, 320.1, 252.3, 254.11, 325; 536/23.1, 23.5

[56] References Cited

FOREIGN PATENT DOCUMENTS

0490410A1  6/1992  European Pat. Off. .

OTHER PUBLICATIONS

Leung et al., Endocrinology, vol. 119, p. 12, 1986.
Coleman et al., Comprehensive Medicinal Chemistry, vol. 3, pp. 643–659, 1989.
Masu et al., Nature, vol. 329, p. 836, 1987.
Alm, A. et al., PhXA34, a New Potent Ocular Hypotensive Drug "A Study on Dose–Response Relationship and on Aqueous Humor Dynamics in Healthy Volunteers," *Arch. Opthalmol.* 109: 1564–1568 (1991).
Balapure, A.K. et al., "Multiple Classes of Prostaglandin $F_{2\alpha}$ Binding Sites in Subpopulations of Ovine Luteal Cells," *Biol. Reprod.* 41: 385–392 (1989).
Dohlman H., et al., "A Family of Receptors Coupled to Guanine Nucleotide Regulatory Proteins," *Biochem.* 26(10):2657–2664 (1987).
Duncan, R. et al., "Prostaglandin $F_{2\alpha}$ Stimulates Inositol 1,4,5–Trisphosphate and Inositol 1,3,4,5–Tetrakisphosphate Formation in Bovine Luteal Cells," *Endocrinol.* 128(3): 1519–1526 (1991).
Hirata, M. et al., "Cloning and Expression of cDNA for a Human Thromboxane $A_2$ Receptor," *Nature* 349: 617–620 (1991).
Kozak, M., "Compilation and Analysis of Sequences Upstream from the Translational Start Site in Eukaryotic mRNAs," *Nucl. Acids Res.* 12(2): 857–872 (1984).
Muallem, S. et al., "Classification of Prostaglandin Receptors Based on Coupling to Signal Transduction Systems," *Biochem. J.* 263: 769–774 (1989).
Namba, T. et al., "Mouse Thromboxane $A_2$ Receptor: cDNA Cloning Expression and Northern Blot Analysis," *Biochem. Biophys. Res. Comm.* 184(3): 1197–1203 (1992).
Orlicky, D.J., et al., "Identification and Purification of a Bovine Corpora Luteal Membrane Glycoprotein with [$^3$H] Prostaglandin $F_{2A}$ Binding Properties," *Prostaglandins Leukotrienes and Essential Fatty Acids* 41: 51–61 (1990).
Sibley, D. et al., "Regulation of Transmembrane Signaling by Receptor Phosphorylation," *Cell* 48: 913–922 (1987).
Strader, C. et al., "Structural Basis of β–adrenergic Receptor Function," *FASEB J.* 3: 1825–1832 (1989).
Sugimoto, Y. et al., "Cloning and Expression of a cDNA for Mouse Prostaglandin E Receptor $EP_3$ Subtype," *J. Biol. Chem.* 267(10): 6463–6466 (1992).

Primary Examiner—Sally P. Teng
Attorney, Agent, or Firm—Sterne, Kessler, Goldstein, & Fox P.L.L.C.

[57] ABSTRACT

Molecular cloning and expression of a prostaglandin F2α receptor which is linked to the signal transduction pathways via guanine nucleotide binding regulatory (G) proteins and measured by, for example, cAMP, $IP_3$ or intracellular calcium. By constructing cell lines that express a prostaglandin F2α, receptor, the affinities and efficacies of agonist and antagonist drugs with the receptor can be assessed. A recombinant DNA construct includes a vector and a DNA fragment encoding a prostaglandin F2α receptor. A host cell is transformed with a recombinant DNA construct, so that the DNA fragment is expressed and a prostaglandin F2α, receptor is produced. Suitable host systems include eukaryotic and prokaryotic cells, especially mamalian cells such as rat or human. Additionally, for diagnostic purposes, antibodies to a prostaglandin F2α receptor can be prepared by producing all or a portion of the receptor protein and injecting these into various types of mammals. Using the resulting antibodies, expression of an F2α receptor cDNA, i.e. receptor protein in tissue and cells can be measured.

15 Claims, 3 Drawing Sheets

FIG. 1A

```
                TCCACAACGATGTCCATAAACAGTTCCAAG
            -9  ---------+---------+---------+ 20
                AGGTGTTGCTACAGGTATTTGTCAAGGTTC
            -3  S  T  T  M  S  I  N* S  S  K
```

```
        CAGCCGGCGTCCTCTGCAGCTGGACTCATCGCCAACACGACTTGCCAGACGGAGAACCGG
        ---------+---------+---------+---------+---------+---------+ 80
        GTCGGCCGCAGGAGACGTCGACCTGAGTAGCGGTTGTGCTGAACGGTCTGCCTCTTGGCC
    8   Q  P  A  S  S  A  A  G  L  I  A  N* T  T  C  Q  T  E  N  R
```

```
        CTTTCAGTGTTCTTTTCAATAATCTTCATGACGGTGGGGATTGTATCTAACAGCCTGGCC
        ---------+---------+---------+---------+---------+---------+ 140
        GAAAGTCACAAGAAAAGTTATTAGAAGTACTGCCACCCCTAACATAGATTGTCGGACCGG
    28  L  S  V  F  F  S  I  I  F  M  T  V  G  I  V  S  N  S  L  A
```

```
        ATTGCCATCCTCATGAAGGCATATCAGAGATTTAGACGGAAGTCGAAGGCTTCTTTCCTG
        ---------+---------+---------+---------+---------+---------+ 200
        TAACGGTAGGAGTACTTCCGTATAGTCTCTAAATCTGCCTTCAGCTTCCGAAGAAAGGAC
    48  I  A  I  L  M  K  A  Y  Q  R  F  R  R  K  S  K  A  S  F  L
```

```
        CTCTTGGCTAGTGGCCTGGTGATCACAGACTTCTTCGGCCACCTCATCAACGGAGGGATA
        ---------+---------+---------+---------+---------+---------+ 260
        GAGAACCGATCACCGGACCACTAGTGTCTGAAGAAGCCGGTGGAGTAGTTGCCTCCCTAT
    68  L  L  A  S  G  L  V  I  T  D  F  F  G  H  L  I  N  G  G  I
```

```
        GCTGTCTTCGTATACGCTTCTGATAAAGACTGGATCCGCTTCGATCAATCGAACATCCTG
        ---------+---------+---------+---------+---------+---------+ 320
        CGACAGAAGCATATGCGAAGACTATTTCTGACCTAGGCGAAGCTAGTTAGCTTGTAGGAC
    88  A  V  F  V  Y  A  S  D  K  D  W  I  R  F  D  Q  S  N  I  L
```

```
        TGCAGTGTTTTTGGGATCTCCATGGTGTTCTCTGGCTTGTGCCCACTTTTCCTGGGCAGT
        ---------+---------+---------+---------+---------+---------+ 380
        ACGTCACAAAAACCCTAGAGGTACCACAAGAGACCGAACACGGGTGAAAAGGACCCGTCA
    108 C  S  V  F  G  I  S  M  V  F  S  G  L  C  P  L  F  L  G  S
```

```
        ACGATGGCCATTGAGAGGTGCATCGGGGTCACCAACCCTCTATTCCACTCTACAAAGATC
        ---------+---------+---------+---------+---------+---------+ 440
        TGCTACCGGTAACTCTCCACGTAGCCCCAGTGGTTGGGAGATAAGGTGAGATGTTTCTAG
    128 T  M  A  I  E  R  C  I  G  V  T  N  P  L  F  H  S̲  T̲  K̲  I
```

```
        ACGTCTAAGCATGTGAAAATGATACTGAGCGGTGTGTGCATGTTTGCTGTCTTCGTGGCC
        ---------+---------+---------+---------+---------+---------+ 500
        TGCAGATTCGTACACTTTTACTATGACTCGCCACACACGTACAAACGACAGAAGCACCGG
    148 T̲  S̲  K̲  H  V  K  M  I  L  S  G  V  C  M  F  A  V  F  V  A
```

```
        CTGTTGCCCATCCTTGGACACCGAGATTATCAAATCCAAGCATCCAGAACTTGGTGCTTC
        ---------+---------+---------+---------+---------+---------+ 560
        GACAACGGGTAGGAACCTGTGGCTCTAATAGTTTAGGTTCGTAGGTCTTGAACCACGAAG
    168 L  L  P  I  L  G  H  R  D  Y  Q  I  Q  A  S  R  T  W  C  F
```

```
        TACAACACAGAGCACATCGAAGACTGGGAAGACAGGTTCTATCTCTTGTTCTTTTCTTCC
        ---------+---------+---------+---------+---------+---------+ 620
        ATGTTGTGTCTCGTGTAGCTTCTGACCCTTCTGTCCAAGATAGAGAACAAGAAAAGAAGG
    188 Y  N  T  E  H  I  E  D  W  E  D  R  F  Y  L  L  F  F  S  S
```

```
        CTGGGACTCTTAGCTCTTGGCATCTCATTCTCGTGCAACGCCGTCACGGGAGTCACACTT
        ---------+---------+---------+---------+---------+---------+ 680
        GACCCTGAGAATCGAGAACCGTAGAGTAAGAGCACGTTGCGGCAGTGCCCTCAGTGTGAA
    208 L  G  L  L  A  L  G  I  S  F  S  C  N  A  V  T  G  V  T  L
```

FIG. 1A(2)

```
        TTGAGAGTGAAGTTTAGAAGTCAGCAGCACAGGCAAGGCAGGTCTCACCACCTGGAGATG
        ---------+---------+---------+---------+---------+---------+ 740
        AACTCTCACTTCAAATCTTCAGTCGTCGTGTCCGTTCCGTCCAGAGTGGTGGACCTCTAC
228     L  R  V  K  F  R  S  Q  Q  H  R  Q  G  R  S  H  H  L  E  M

GTCATTCAGCTCCTGGCCATAATGTGTGTCTCCTGCGTCTGCTGGAGTCCCTTTCTGGTG
        ---------+---------+---------+---------+---------+---------+ 800
        CAGTAAGTCGAGGACCGGTATTACACACAGAGGACGCAGACGACCTCAGGGAAAGACCAC
248     V  I  Q  L  L  A  I  M  C  V  S  C  V  C  W  S  P  F  L  V

ACGATGGCCAACATTGCAATCAATGGAAATAATTCCCCAGTGACCTGTGAGACGACGCTC
        ---------+---------+---------+---------+---------+---------+ 860
        TGCTACCGGTTGTAACGTTAGTTACCTTTATTAAGGGGTCACTGGACACTCTGCTGCGAG
268     T  M  A  N  I  A  I  N  G  N* N  S  P  V  T  C  E  T  T  L

TTTGCTCTCCGAATGGCAACCTGGAACCAGATATTAGACCCCTGGGTCTACATTCTGCTA
        ---------+---------+---------+---------+---------+---------+ 920
        AAACGAGAGGCTTACCGTTGGACCTTGGTCTATAATCTGGGGACCCAGATGTAAGACGAT
288     F  A  L  R  M  A  T  W  N  Q  I  L  D  P  W  V  Y  I  L  L

CGGAAGGCTGTCCTTAGGAACCTGTACAAGCTTGCCAGTCGCTGCTGTGGAGTGAACATC
        ---------+---------+---------+---------+---------+---------+ 980
        GCCTTCCGACAGGAATCCTTGGACATGTTCGAACGGTCAGCGACGACACCTCACTTGTAG
308     R  K  A  V  L  R  N  L  Y  K  L  A  S  R  C  C  G  V  N  I

ATCAGCTTGCACATCTGGGAACTCAGCTCCATCAAGAATTCCTTAAAGGTTGCTGCTATC
        ---------+---------+---------+---------+---------+---------+ 1040
        TAGTCGAACGTGTAGACCCTTGAGTCGAGGTAGTTCTTAAGGAATTTCCAACGACGATAG
328     I  S  L  H  I  W  E  L  S  S  I  K  N  S  L  K  V  A  A  I
                                       ‾‾‾‾‾‾‾     ‾‾‾‾‾‾

TCTGAGTCACCGGCTGCAGAGAAGGAGAATCAGCAAGCATCTAGTGAGGCTGGACTGTAA
        ---------+---------+---------+---------+---------+---------+ 1100
        AGACTCAGTGGCCGACGTCTCTTCCTCTTAGTCGTTCGTAGATCACTCCGACCTGACATT
348     S  E  S  P  A  A  E  K  E  N  Q  Q  A  S  S  E  A  G  L  *

GTCAATGCA
        --------- 1109
        CAGTTACGT
        V  N  A
```

Name: RatFP2α = 3                                   FIG. 1B
      HumTXA2 = 2
      MouseEP3 = 1

```
              1                                                        50
    3    .MSINSSKQP ASSAAGLIAN TTCQTENRLS VFFSIIFMTV GIVSNSLAIA
    2    .MWPNGS..S LGPCFRPTNI TLEERRLIAS PWFAASFCVV GLASNLLALS
    1    MASMWAPEHS AE.AHSNLSS TTDDCGSV.S VAFPITMMVT GFVGNALAML
                                          --------tm1---------

51                                                       100
    3    ILMKAYQRFR RKSKASFLLL ASGLVITDFF GHLINGGIAV FVYASDKDWI
    2    VLAGA.RQGG SHTRSSFLTF LCGLVLTDFL GLLVTGTIVV SQHAALFEWH
    1    LVSRSYRRRE SKRKKSFLLC IGWLALTDLV GQLLTSPVVI LVYLSQRRWE
         ------                -----------tm2--------

101                                                      150
    3    RFDQSNILCS VFGISMVFSG LCPLFLGSTM AIERCIGVTN PLFHSTKITS
    2    AVDPGCRLCR FMGVVMIFFG LSPLLLGAAM ASERYLGITR PFSRPAVASQ
    1    QLDPSGRLCT FFGLTMTVFG LSSLLVASAM AVERALAIRA PHW...YASH
                    ------------tm3-----------

151                                                      200
    3    ..KHVKMILS GVCMFAVFVA LLPILGHRDY QIQASRTWCF YNTEHIE...
    2    RRAWATVGL. .VWAAALALG LLPLLGVGRY TVQYPGSWCF LTLGA.....
    1    MKTRATPVLL GVWLSVLAFA LLPVLGVGRY SVQWPGTWCF ISTGPAGNET
                    ------------tm4-----------

201                                                      250
    3    ....DWEDRF YLLFFSSLGL LALGISFSCN AVTGVTLLRV KFRSQQHRQG
    2    ....ESGDVA FGLLFSMLGG LSVGLSFLLN TVSVATLCHV .YHGQEAAQQ
    1    DPAREPGSVA FASAFACLGL LALVVTFACN LATIKALVSR .CRAKAAVSQ
                   ---------------tm5-------------

251                                                      300
    3    RSHH.....L EMVIQLLAIM CVSCVCWSPF LVTMANIAIN GN........
    2    RPRDSE...V EMMAQLLGIM VVASVCWLPL LVFIAQTVLR NPPAMSPAGQ
    1    SSAQWGRITT ETAIQLMGIM CVLSVCWSPL LIMMLKMIFN QMSVEQCKTQ
                                ---------------tm6----------

301                                                      350
    3    NSPVT.CETT LFALRMATWN QILDPWVYIL LRKAVLRNLY KLASRCCGVN
    2    LSRTTE.KEL LIYLRVATWN QILDPWVYIL FRRAVLRRL. ..........
    1    MGKEKECNSF LIAVRLASLN QILDPWVYLL LRKILLRKFC ..........
                              ------------tm7-------------

351                            391
    3    IISLHIWELS SIKNSLKVAA ISESPAAEKE NQQASSEAGL *
    2    ....QPR.LS TRPRSLSLQP QLTQRSGLQ*. ..........  .
    1    ....QIRDHT NYASSSTSLP CPGSSALMWS DQLER*..... .
```

DNA ENCODING A PROSTAGLANDIN F2β RECEPTOR, A HOST CELL TRANSFORMED THEREWITH AND AN EXPRESSION PRODUCT THEREOF

BACKGROUND OF THE INVENTION

1. Technical Field

The present invention relates, in general, to the molecular cloning and expression of a receptor protein, and, in particular, to a prostaglandin F2α receptor and fragments thereof linked to the activation of second messengers as measured, for example, by cAMP, $IP_3$ or intracellular calcium. The invention further relates to a DNA sequence encoding a prostaglandin F2α receptor, to a recombinant DNA molecule that includes such a DNA sequence and to cells transformed therewith. The invention also relates to antibodies directed against the F2α receptor and to a method of detecting an F2α receptor with the antibody. The invention further relates to a method of detecting the presence of an F2α receptor encoding a DNA fragment in a sample, the use of transformed cells for screening drugs, as well as to drugs prepared using such a screening method.

2. Background Information

Prostaglandin F2α receptors belong to a large class of hormone receptors which are linked to their signal transduction pathways via guanine nucleotide binding regulatory (G) proteins. Such receptors are amongst the most intensively studied receptor systems. Prostaglandin receptors have been classically defined as being linked to the stimulation of second messengers and measured by cyclic AMP (cAMP), inositol 3-phosphate ($IP_3$) or intracellular calcium and are coupled with a G regulatory protein (Muallem, Biochem. J. 263: 769–774 (1989)). In contrast, activation of prostaglandin receptors may result in various responses, including inhibition of adenylyl cyclase activity, inhibition of phosphatidylinositol turnover and inhibition of $Ca^{2+}$ mobilization (Muallem, Biochem. J. 263: 769–774 (1989), and Duncan, Endocrinology 128: 1519–1526 (1991)). Evidence has also accumulated suggesting heterogeneity in the category of receptors (Balapure, Biol. Reprod. 41: 385–392 (1989)).

Two prostaglandin receptors have previously been cloned, viz. the human and mouse thromboxane A2 receptor and the mouse prostaglandin $E_3$ receptor (Hirata, Nature 349: 617–620 (1991); Namba, BBRC 184: 1197–1203 (1992); and Sugimoto, J. Biol. Chem. 267: 6463–6466 (1992), respectively).

Prostaglandin F2α receptors are extremely important from a clinical therapeutic viewpoint. Drugs which activate (agonists) these receptors may be used to treat glaucoma (Alm, Arch. Ophthalmol. 109:1564–1568 (1991)), whereas drugs which block (antagonists) prostaglandin F2α receptors may be used therapeutically to treat pathological conditions, e.g. in the lungs and uterus. It may be of pharmaceutical value to be able to titer endogenous prostaglandin F2α with a solubilized receptor as well as to use an immobilized receptor in the purification of a ligand and its analogs. Despite their clinical utility, one problem with the prostaglandin F2α agonist and putatively antagonist drugs currently available, is that they have many side effects, like many other drugs which work through interaction with receptors. These side effects are predominantly due to a lack of receptor specificity. That is, the drug in use interacts not only with prostaglandin F2α receptors but with other receptors as well, see e.g. Muallem, Biochem. J. 263; 769–774 (1989).

A major goal of clinical pharmacology and the pharmaceutical industry is the development of more selective drugs with greater efficacy than those currently in use. Impediments to this process are the low abundance of prostaglandin F2α receptor protein available to study in eye tissue and the lack of suitable homogeneous model systems of the receptors with which to screen drugs against.

SUMMARY OF THE INVENTION

The present invention seeks to provide a solution to this problem by a novel approach which comprises cloning cDNAs encoding prostaglandin F2α receptors, constructing eukaryotic expression vectors containing these cDNAs, and creating a series of stably transfected mammalian cell lines or prokaryotic cells which express functional prostaglandin F2α receptors in high abundance. These cell lines, which would express a homogeneous population of prostaglandin F2α receptors, can be used by the pharmaceutical industry or others to screen drugs and study the prostaglandin F2α receptors using a variety of biochemical, physiological and pharmacological techniques.

To accomplish this goal, we have isolated a cDNA encoding a rat prostaglandin F2α receptor subtype linked to the activation of second messengers as measured by e.g. cAMP, $IP_3$ or intracellular calcium. This cDNA encoding an F2α receptor is inserted into different eukaryotic and prokaryotic expression vectors and used in the construction of various mammalian cell lines expressing this functional protein. Resulting F2α receptor-expressing cell lines can be used to investigate the affinities and efficacies of agonist and antagonist drugs with an F2α receptor using various techniques, such as radioligand binding and second messenger assays.

One aspect of the present invention therefore relates to an F2α receptor that is linked to the stimulation of second messengers, such as cAMP, $IP_3$ or intracellular calcium, and that couples with guanine nucleotide binding regulatory (G) proteins, when present.

Another aspect of the present invention relates to a DNA fragment encoding the above described prostaglandin F2α x receptor.

A further aspect of the present invention relates to a recombinant DNA construct or molecule comprising a vector and the above-described DNA fragment.

Yet another aspect of the present invention relates to a host cell transformed with the above described recombinant DNA construct.

In another aspect, the present invention relates to a process of producing the above-described prostaglandin F2α receptor. The method comprises culturing the above-mentioned host cell under conditions such that the F2α receptor encoding DNA fragment is expressed and a prostaglandin F2α receptor is produced.

Still another aspect of the invention relates to an antibody directed against the F2α receptor.

Another aspect of the invention relates to a method of detecting the presence of an F2α receptor in a sample by contacting the sample with such an antibody.

Still another aspect of the invention relates to a method of detecting the presence in a sample of a DNA fragment encoding an F2α receptor by contacting the sample with a DNA probe comprising a DNA fragment encoding an F2α receptor protein or polypeptide to hybridize the DNA fragment thereto.

Yet another aspect of the invention relates to a method of screening drugs for F2α receptor activating or blocking activity by contacting the above-mentioned transformed host cell with the drugs.

Another aspect of the invention relates to a method of preparing a drug, which method includes screening drug candidates for F2α receptor activating or blocking activity.

A further aspect of the invention relates to a drug, the preparation of which included screening drug candidates for F2α receptor activating or blocking activity.

BRIEF DESCRIPTION OF THE DRAWINGS

FIGS. 1A and 1B show the sequence of a rat prostaglandin F2α receptor (SEQ ID NO:1 and 2) and comparison with the sequences of other G protein-coupled receptors (SEQ ID NO:3-5).

FIG. 1A shows the nucleotide sequence of an F2α receptor (SEQ ID NO:1) along with the deduced amino acid sequence of the longest open reading frame (SEQ ID NO:2). The nucleotide sequence is numbered from the putative initiator methionine and indicated at the left of each line while the amino acid numbers are indicated at the right of each line. The postulated N-linked glycosylation sites are indicated by an asterisk. The potential site for phosphorylation by the cAMP-dependent protein kinase is underlined.

FIG. 1B shows a comparison of a prostaglandin F2α receptor amino acid sequence with that of other known prostaglandin receptors. Amino acid sequences of the human thromboxane $A_2$ receptor (2) (SEQ ID NO:4) and the mouse prostaglandin $E_3$ receptor (1) ( SEQ. ID No:3) were aligned to optimize the homology with a rat prostaglandin F2α receptor sequence (3) (SEQ ID NO:5). Amino acid identities between the F2α and the two other prostaglandin receptors are indicated with bold type. The putative transmembrane (TM) regions are indicated by the dashed lines.

DETAILED DESCRIPTION OF THE INVENTION

The present invention relates to a prostaglandin F2α receptor that is linked to the activation of second messengers, for example, as measured by cAMP, $IP_3$ or intracellular calcium, and that is coupled with the guanine nucleotide binding regulatory (G) protein, when present. The invention further relates to DNA sequences (fragments) encoding all, or parts of an F2α receptor protein. The invention also relates to a recombinant construct containing such DNA sequences, to cells transformed therewith, and to methods of expressing the receptor gene. Also, the invention relates to an antibody to the F2α receptor and the use of the antibody for detecting the presence of an F2α receptor in the sample. The invention further relates to a method for detecting the presence in a sample of a DNA fragment encoding an F2α receptor. The invention also relates to a method for screening drugs by means of the transformed cells. Furthermore, the invention relates to a method of preparing drugs, which method includes such a screening procedure, as well as to drugs prepared by the method.

The F2α receptor protein or polypeptide of the present invention is one of a large class of receptors which are linked to their signal transduction via guanine nucleotide binding regulatory proteins. Specifically, an F2α receptor of the invention is linked to the activation of second messengers as measured by, for example, cAMP, $IP_3$ or intracellular calcium, and couples with the G regulatory protein, when present (e.g. prokaryotic systems lack G regulatory proteins).

The term "F2α receptor" as used herein in the context of the present invention is to be understood in a broad sense.

Thus, an F2α receptor can have the complete sequence given in FIG. 1A (SEQ ID NO:2), or can have the amino acid sequence of a molecule having substantially the same second messenger properties as measured by e.g. cAMP, $IP_3$ or intracellular calcium, pharmacological properties, and G regulatory protein coupling properties of the molecule corresponding to FIG. 1A ( SEQ. ID NO:2) (for example, allelic variations of the F2α receptor protein). Alternatively, an F2α receptor protein (or polypeptide) of the invention can have an amino acid sequence corresponding to any active portion or parts of a protein depicted in FIG. 1A (SEQ ID NO:2) (or allelic variations thereof). As an example, an F2α receptor protein (or polypeptide) can have an amino acid sequence corresponding to an epitope of the FIG. 1A sequence (SEQ ID NO:2) (or an allelic variation thereof).

The F2α receptor protein or polypeptide can be present in a substantially pure form, that is, in a form substantially free of proteins and nucleic acids with which it is normally associated. An F2α receptor protein can be purified using protocols known in the art. An F2α receptor protein can also be used as an antigen, in protocols known in the art, to produce antibodies thereto, both monoclonal and polyclonal.

As indicated above, the present invention also relates to DNA sequences (including cDNA sequences) that encode the entire amino acid sequence given in FIG. 1A (SEQ ID NO:2) (the specific cDNA sequence given in FIG. 1A being only one example), or any portion thereof. The DNA sequences to which the invention relates also include those encoding proteins (or polypeptides) having substantially the same second messengers properties as measured by, for example, cAMP, $IP_3$ or intracellular calcium, pharmacological properties, and G regulatory protein coupling properties of an F2α receptor (for example, allelic forms of the sequence of FIG. 1A (SEQ ID NO:2)).

Further, the present invention relates to a recombinant DNA construct that includes a vector and a DNA sequence as described above (advantageously, a DNA sequence encoding the receptor shown in FIG. 1A or a receptor having the same second messenger properties as measured by, for example, cAMP, $IP_3$ or intracellular calcium, pharmacological properties, and G protein coupling properties of that protein).

The vector can take the form of a virus or a plasmid vector (for example, lambda ZAP II). The DNA sequence can be present in the vector operably linked to regulatory elements, including, for example, a promoter. The recombinant construct can be suitable for transforming prokaryotic or eukaryotic cells, or advantageously, mammalian cells.

The present invention also relates to a host cell transformed with the above described recombinant construct. The host can be prokaryotic (for example, bacterial), lower eukaryotic (i.e., fungal, including yeast) or higher eukaryotic (i.e., all mammalian, including but not limited to rat and human). For instance, stable transformations are accomplished into Chinese hamster ovary cells (CHO-cells). Transformation can be effected using methods known in the art. The transformed host cells can be used as a source for the DNA sequence described above (which sequence constitutes part of the recombinant construct). When the recombinant receptor takes the form of an expression system, the transformed cells can be used as a source for the above-described receptor.

The presence of an F2α receptor protein can be detected in a sample (for instance, tissue from a human or other mammal, or a cell culture) by contacting the sample with an antibody to the receptor. The detection of the presence or absence of a complex formed between the receptor and the antibody may be accomplished by methods well known in the art. The presence of a DNA segment encoding an F2α receptor protein can be detected in a sample (for instance, tissue from a human or other mammal, or a cell culture) by contacting the sample with a DNA probe that is comprised of the DNA segment or fragments thereof. Using methods well known in the art and under conditions such that hybridization will occur, a complex can be formed between the probe and the DNA segment from the sample. Detection of the presence or absence of the complex may be accomplished by methods well known in the art.

A prostaglandin F2α receptor protein and nucleic acid sequences of the present invention can be used both in a research setting (for example, to facilitate an understanding of receptor protein mechanisms) and in a clinical setting (for example, to use as a model system of the receptor with which to screen agonist and antagonist drugs against). For instance, therapeutic drugs designed to interact with prostaglandin F2α receptors often have side effects, due to lack of receptor specificity. A cell line expressing an F2α receptor can be used to investigate the affinities and efficacies of agonist and antagonist drugs with an F2α receptor using various techniques, such as radioligand binding and second messenger assays. The activity of the drug-treated cell can be compared to a control cell to evaluate the activation or blocking of an F2α receptor.

For diagnostic purposes, expression of an F2α receptor cDNA in cells can be measured using known methods. To accomplish this, antibodies to an F2α receptor (prepared by producing all or portions of an F2α receptor protein and injecting these into various types of animals, e.g., rabbits, sheep, goats or mice) can be used.

The invention is described in further detail below and in the following non-limiting Example with regard to the isolation and characterization of cDNA clones for an F2α receptor.

Isolation and characterization of cDNA clones for a prostaglandin F2α receptor (i) Cloning and sequencing analyses of prostaglandin F2α receptor CDNA In order to clone a prostaglandin F2α receptor, hereinafter for brevity often called FP-receptor, linked to second messenger activation as measured by e.g. cAMP, IP$_3$ or intracellular calcium, the PCR method was used to selectively amplify cDNA sequences from mRNA purified from rat corpora lutea. Ovine and bovine corpora lutea have previously been shown to express this receptor subtype (Balapure, Biol. of Reproduction 41: 385–392 (1989) and Orlicky, Prostaglandins Leukotrines and Essential Fatty Acids 41: 51–61 (1990)). A commercial cDNA library was used to obtain cDNA from rat corpora lutea. PCR amplification was performed with a pair of highly degenerate primers (SEQ ID NOS:6 and 7) derived from the second and seventh and third and sixth transmembrane regions of previously cloned seven transmembrane receptor superfamily members. This process resulted in the amplification of several cDNA fragments.

These fragments were preliminarily characterized by DNA sequence analysis. One of these fragments was found to exhibit considerable sequence homology to related previously cloned G protein-coupled receptors and was subsequently used to screen the rat corpora lutea cDNA library in order to isolate a full-length clone. Twenty-four cDNA clones with insert sizes ranging from about 1.7 to 3.3 kb were isolated, all of which strongly hybridized with the $^{32}$P-labelled PCR probe on Southern analysis. One of these clones with an insert of about 3 kb was sequenced and found to exhibit more than 55% amino acid sequence homology to related receptors in the coding regions of the sequence. The homology is about the same in all combinations, in spite of the different receptors and also the in one case different species, human vs. rat. The nucleotide and deduced amino acid sequences for clone FP are shown in FIG. 1A (SEQ ID NOS:1 and 2). The longest open reading frame in this cDNA codes for a 366 residue protein with a theoretical molecular weight of 40.65 kDa.

Although there are neighbouring sequences with ATG in this reading frame similar to Kozak's consensus initiation sequence (Kozak, Nucleic Acids Res., 12:857–872 (1984)), the Met codon at position 1 actually provides the most probable site. (FIG. 1A (SEQ ID NO:1)).

Hydrophobicity analysis of the translated protein reveals seven clusters of about 20–25 hydrophobic residues, predicted to represent transmembrane-spanning domains, connected by three extracellular and three intracellular loops. This pattern is similar to that observed for other cloned G protein-coupled receptors where the NH$_2$ terminus is proposed to be extra-cellular and the COOH terminus projects into the cytoplasm (Dohlman, Biochemistry, 26:2657–2664 (1987)). The NH$_2$ terminus contains two consensus site for N-linked glycosylation while the predicted third cytoplasmic loop exhibits one. Consensus recognition sites for phosphorylation by the cAMP-dependent protein kinase are found in the cytoplasmic loops and the carboxy tail. In addition, the long COOH terminus contains several serine residues possibly representing additional sites for 30 regulatory phosphorylation. These phosphorylations are proposed for the regulation of transmembrane signaling and desensitization of the receptor (Sibley, Cell. 48:913–922 (1987)).

(ii) Characterization of the amino acid sequences for a prostaglandin F2α receptor clone A comparison of the deduced amino acid sequence for the cDNA clones with the sequences of various prostaglandin receptors is shown in FIG. 1B (SEQ ID NOS:3–5). As can be seen, the regions of highest identity appear to occur within the predicted transmembrane spanning domains. Within these regions, the FP receptor protein exhibits the highest sequence homologies with the rat prostaglandin E3 and thromboxane A2 receptor, mouse and human. The NH$_2$ and COOH termini and the extracellular and intracellular loops are significantly more divergent among these receptors. It is interesting to note that within the third putative transmembrane domain of FP, there is no conserved aspartate residue which is common to all biogenic amine receptors that have been sequenced thus far (Strader, FASEB J., 3: 1825–1832 (1989)). Moreover, the fifth transmembrane spanning domain of FP also contains two serine residues which are conserved among catecholamine receptors and are critical for the recognition of agonist ligands possessing a catechol group (Strader, FASEB J., 3: 1825–1832 (1989)).

Furthermore, with primers (SEQ ID NOS:8 and 9) derived from the sequence encoding the F2α receptor and using PCR in cDNA libraries from human tissue expected to express the F2α receptor, fragments of the correct size were found, showing between them identical restriction fragments. The tissues were e.g the eye, ovary, uterus and kidney.

These observations suggest that the F2α receptor cDNA clone of the present invention encodes a receptor for an endogenous prostaglandin ligand.

EXAMPLE

Isolation and characterization of cDNA clones for a new G protein coupled receptor In order to clone an FP-receptor, the polymerase chain reaction (PCR) method was used to amplify cDNA sequences from Rat corpora lutea cDNA library in the lambda ZAP^C II vector, (Stratagene, Catalogue No. 936504). 1×10^6 pfu of the library were amplified and lambda DNA was prepared as described in Current Protocols in Molecular Biology (1990) 1.13.1–1.13.3. 50 ng of the lambda DNA were submitted to 45 cycles of PCR amplification in a total reaction volume of 25 μl with 1 μM each of the two primers:

TM206: 5' ATI I(CT)(CG) (TA)I(TC) (TC)TG GCI ITI ICC GAT 3' (SEQ ID NO:6) and

TM710: 5' C(GT)(AG) AAI AGI AT(AG) TAI ACC CAI GGG TC 3' (SEQ ID NO:7); and 200 μM dNTPs and 2 u of Taq DNA polymerase (Perkin Elmer-Cetus, U.S.A.). The timing used was 45 seconds (in the first cycle 3 minutes) at 95 degrees Celsius, 3 minutes at 50 degrees Celsius and 3 minutes at 72 degrees Celsius. The 72 degrees Celsius step was extended with 6 seconds for each cycle. The reaction products were purified by electrophoresis in 1% LMP agarose (BioRad Laboratories, Richmond, Calif., U.S.A., Catalogue No. 162-0020). Individual bands were excised from the gel and were submitted to 20 cycles of PCR-amplification in a total reaction volume of 20 μl with 100 μM of each of the same two primers as above, i.e.:

TM206: 5' ATI I(CT)(CG) (TA)I(TC) (TC)TG GCI ITI ICC GAT 3' (SEQ ID NO:6) and

TM710: 5' C(GT)(AG) AAI AGI AT(AG) TAI ACC CAI GGG TC 3' (SEQ ID NO:7); and 200 μM of dNTPs and 2,5 u of Taq DNA polymerase. The timing used was identical to the timing described above.

The reaction products were ligated into the vector PCR1000 according to the instructions of the TA Cloning Kit (Invitrogen Corporation, U.S.A., Catalogue no. K2000-1). The obtained plasmid was called pKGE858. Mini preparation of plasmid DNA was done with a Qiagene-tip 100 kit (Diagene-GmbH, Germany). Insert sequencing was performed according to methods well known in the art. Thus, the cDNA inserts were sequenced with primers homologous to regions on the M13 multiple cloning site. To reveal the whole cDNA sequences, a gene walking strategy was used. All sequence analyses were performed on an Applied Biosystem Model 373A DNA sequencing system (Applied Biosystems Inc., U.S.A.) according to Applied Biosystems' protocol for their Taq Dye Dioxy Terminator cycle sequencing kit. The generated primary data were processed on a VAX computer using the sequence analysis programs from Genetics Computer Group Inc., Madison, U.S.A. (Devereux, Nucleic Acids Research 12 (1): 387–395 (1984)). One of the inserts was found to exhibit a sequence homology to related receptors (the human thromboxane A2 receptor and later on also to other cloned prostaglandin receptors; Hirata, Nature 349: 617–620 (1991), Sugimoto, J. Biol. Chem. 267: 6463–6466 (1992), and Namba BBRC 184: 1197–1203 (1992)). This insert was subsequently used as a probe to screen the rat Corpora lutea cDNA library to isolate a full-length clone. 1×10^6 recombinants from the rat Corpora lutea cDNA library, constructed in the Lambda ZAP II vector, were screened with the insert described above. The probe consisting of the NotI/HindIII 600 bp fragment of the plasmid pKGE858 obtained above was labelled with Amershams Megaprime DNA labelling system (Amersham, England, RPN1607). Duplicate nitrocellulose filters (Hybond-N, (Amersham, England) were hybridized in 10% (w/v) dextran sulfate, 1% sodium dodecyl sulfate, 1M sodium chloride and 100 μg/ml sonicated salmon sperm DNA (Boehringer Mannheim, Germany) with the probe described above for 16 h at 65 degrees Celsius. High stringency washing of the filters was performed with 2× SSC and 1% sodium dodecyl sulfate at 65 degrees Celsius for 30 minutes. Positively hybridizing phage clones were further purified by rescreening using the same probe as in the initial screening. 25 positively hybridizing purified phage clones were expanded in *E. coli* XL1-Blue (Stratagene, U.S.A.), and the resulting phage stocks used to prepare cDNA-containing pBluescript plasmids by phagemid excision using helper phage R408 according to the Stratagene protocol. Plasmid DNA was prepared with Qiagene-tip 100 (Diagene GmbH, Germany) and further analyzed by restriction analysis. The four plasmids with the longest inserts were analyzed by DNA sequencing methods well known in the art. The DNA sequence of one of these inserts is shown in FIG. 1A.

To detect the F2α receptor in tissues expected to express the same, primers derived from the sequence encoding the F2α receptor in transmembrane (TM) regions VI and VII were used. The primer sequence in TM VI was:

5'-CCAGCTTCTGGGTATAATGTGTGT-3' (SEQ ID NO:8)

and the primer sequence in TM VII was:

5'-AGCAGSATATARGCCCAGGGGTCCAAGATCT-GGTTCCRGGWTGCCATKCG -3' (SEQ ID NO:9).

The amplified product had a size of 173 bp. The PCR reactions were performed as above. By cutting the fragment with the restriction enzyme HaeIII, which is unique in the human fragment, two bands were obtained with the sizes 100 and 73 bp, respectively. Fragments from the cDNA libraries all showed these characteristics.

The entire contents of all references cited herein above are incorporated by reference.

While the foregoing invention has been described in some detail for purposes of clarity and understanding, it will be clear to one skilled in the art from a reading of this disclosure that various changes in form and detail can be made without departing from the true scope of the invention.

---

We claim:

1. A purified prostaglandin F2α receptor comprising amino acids 1 to 366 of SEQ ID NO:2.

2. A purified nucleic acid comprising a nucleotide sequence encoding a prostaglandin F2α receptor, wherein said sequence comprises nucleotides encoding the amino acid sequence of amino acids 1 to 366 of SEQ ID NO:2.

3. The purified nucleic acid according to claim 2, wherein said nucleotide sequence encoding said amino acid sequence is nucleotides 10 to 1107 of SEQ ID NO: 1.

4. A host cell transformed or transfected with a DNA molecule comprising a nucleotide sequence encoding the amino acid sequence of amino acids 1 to 366 of SEQ ID NO:2.

5. The host cell according to claim 4, wherein said nucleotide sequence encoding said amino acid sequence is nucleotides 10 to 1107 of SEQ ID NO:1.

6. The host cell according to claim 4 or 5, wherein said host cell is a eukaryotic host cell.

7. The host cell according to claim 4 or 5, wherein said host cell is a prokaryotic host cell.

8. A method of producing a prostaglandin F2α receptor, said method comprising culturing the host cell according to claim 4 or 5 under conditions such that said nucleotide sequence is expressed and said receptor is produced.

9. A vector comprising a nucleotide sequence encoding the amino acid sequence of amino acids 1 to 366 of SEQ ID NO:2.

10. The vector according to claim 9, wherein said nucleotide sequence encoding said amino acid sequence is nucleotides 10 to 1107 of SEQ ID NO:1.

11. The vector according to claim 9 or 10, wherein said vector is a eukaryotic expression vector.

12. The vector according to claim 9 or 10, wherein said vector is a prokaryotic expression vector.

13. A host cell transformed or transfected with the vector according to claim 9 or 10.

14. The host cell according to claim 13, wherein said host cell is a eukaryotic host cell.

15. The host cell according to claim 13, wherein said host cell is a prokaryotic host cell.

* * * * *

UNITED STATES PATENT AND TRADEMARK OFFICE
CERTIFICATE OF CORRECTION

PATENT NO. : 5,750,369
DATED : May 12, 1998
INVENTOR(S) : Lake et al.

It is certified that error appears in the above-identified patent and that said Letters Patent is hereby corrected as shown below:

On the title page and column 1, line 1, item [54],
  "F28" should read --$F2\alpha$--.

Signed and Sealed this

Twenty-seventh Day of October, 1998

Attest:

BRUCE LEHMAN

*Attesting Officer*     *Commissioner of Patents and Trademarks*

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
　　　　( A ) LENGTH: 1119 base pairs
　　　　( B ) TYPE: nucleic acid
　　　　( C ) STRANDEDNESS: double (D) TOPOLOGY: linear (ii) MOLECULE TYPE: cDNA (ix) FEATURE:
    (A) NAME/KEY: CDS
    (B) LOCATION: 1..1107

(ix) FEATURE:
    (A) NAME/KEY: mat_peptide
    (B) LOCATION: 10..1107

(xi) SEQUENCE DESCRIPTION: SEQ ID NO:1:

```
TCC ACA ACG ATG TCC ATA AAC AGT TCC AAG CAG CCG GCG TCC TCT GCA        48
Ser Thr Thr Met Ser Ile Asn Ser Ser Lys Gln Pro Ala Ser Ser Ala
 -3          1               5                  10

GCT GGA CTC ATC GCC AAC ACG ACT TGC CAG ACG GAG AAC CGG CTT TCA        96
Ala Gly Leu Ile Ala Asn Thr Thr Cys Gln Thr Glu Asn Arg Leu Ser
         15                  20                  25

GTG TTC TTT TCA ATA ATC TTC ATG ACG GTG GGG ATT GTA TCT AAC AGC       144
Val Phe Phe Ser Ile Ile Phe Met Thr Val Gly Ile Val Ser Asn Ser
 30                  35                  40                  45

CTG GCC ATT GCC ATC CTC ATG AAG GCA TAT CAG AGA TTT AGA CGG AAG       192
Leu Ala Ile Ala Ile Leu Met Lys Ala Tyr Gln Arg Phe Arg Arg Lys
                 50                  55                  60

TCG AAG GCT TCT TTC CTG CTC TTG GCT AGT GGC CTG GTG ATC ACA GAC       240
Ser Lys Ala Ser Phe Leu Leu Leu Ala Ser Gly Leu Val Ile Thr Asp
             65                  70                  75

TTC TTC GGC CAC CTC ATC AAC GGA GGG ATA GCT GTC TTC GTA TAC GCT       288
Phe Phe Gly His Leu Ile Asn Gly Gly Ile Ala Val Phe Val Tyr Ala
         80                  85                  90

TCT GAT AAA GAC TGG ATC CGC TTC GAT CAA TCG AAC ATC CTG TGC AGT       336
Ser Asp Lys Asp Trp Ile Arg Phe Asp Gln Ser Asn Ile Leu Cys Ser
 95                 100                 105

GTT TTT GGG ATC TCC ATG GTG TTC TCT GGC TTG TGC CCA CTT TTC CTG       384
Val Phe Gly Ile Ser Met Val Phe Ser Gly Leu Cys Pro Leu Phe Leu
110                 115                 120                 125

GGC AGT ACG ATG GCC ATT GAG AGG TGC ATC GGG GTC ACC AAC CCT CTA       432
Gly Ser Thr Met Ala Ile Glu Arg Cys Ile Gly Val Thr Asn Pro Leu
                130                 135                 140

TTC CAC TCT ACA AAG ATC ACG TCT AAG CAT GTG AAA ATG ATA CTG AGC       480
Phe His Ser Thr Lys Ile Thr Ser Lys His Val Lys Met Ile Leu Ser
            145                 150                 155

GGT GTG TGC ATG TTT GCT GTC TTC GTG GCC CTG TTG CCC ATC CTT GGA       528
Gly Val Cys Met Phe Ala Val Phe Val Ala Leu Leu Pro Ile Leu Gly
        160                 165                 170

CAC CGA GAT TAT CAA ATC CAA GCA TCC AGA ACT TGG TGC TTC TAC AAC       576
His Arg Asp Tyr Gln Ile Gln Ala Ser Arg Thr Trp Cys Phe Tyr Asn
175                 180                 185

ACA GAG CAC ATC GAA GAC TGG GAA GAC AGG TTC TAT CTC TTG TTC TTT       624
Thr Glu His Ile Glu Asp Trp Glu Asp Arg Phe Tyr Leu Leu Phe Phe
190                 195                 200                 205

TCT TCC CTG GGA CTC TTA GCT CTT GGC ATC TCA TTC TCG TGC AAC GCC       672
Ser Ser Leu Gly Leu Leu Ala Leu Gly Ile Ser Phe Ser Cys Asn Ala
                210                 215                 220

GTC ACG GGA GTC ACA CTT TTG AGA GTG AAG TTT AGA AGT CAG CAG CAC       720
Val Thr Gly Val Thr Leu Leu Arg Val Lys Phe Arg Ser Gln Gln His
            225                 230                 235

AGG CAA GGC AGG TCT CAC CAC CTG GAG ATG GTC ATT CAG CTC CTG GCC       768
Arg Gln Gly Arg Ser His His Leu Glu Met Val Ile Gln Leu Leu Ala
        240                 245                 250

ATA ATG TGT GTC TCC TGC GTC TGC TGG AGT CCC TTT CTG GTG ACG ATG       816
Ile Met Cys Val Ser Cys Val Cys Trp Ser Pro Phe Leu Val Thr Met
```

```
                    255                         260                         265
GCC  AAC  ATT  GCA  ATC  AAT  GGA  AAT  AAT  TCC  CCA  GTG  ACC  TGT  GAG  ACG        864
Ala  Asn  Ile  Ala  Ile  Asn  Gly  Asn  Asn  Ser  Pro  Val  Thr  Cys  Glu  Thr
270                      275                      280                      285

ACG  CTC  TTT  GCT  CTC  CGA  ATG  GCA  ACC  TGG  AAC  CAG  ATA  TTA  GAC  CCC        912
Thr  Leu  Phe  Ala  Leu  Arg  Met  Ala  Thr  Trp  Asn  Gln  Ile  Leu  Asp  Pro
                    290                      295                      300

TGG  GTC  TAC  ATT  CTG  CTA  CGG  AAG  GCT  GTC  CTT  AGG  AAC  CTG  TAC  AAG        960
Trp  Val  Tyr  Ile  Leu  Leu  Arg  Lys  Ala  Val  Leu  Arg  Asn  Leu  Tyr  Lys
               305                      310                      315

CTT  GCC  AGT  CGC  TGC  TGT  GGA  GTG  AAC  ATC  ATC  AGC  TTG  CAC  ATC  TGG       1008
Leu  Ala  Ser  Arg  Cys  Cys  Gly  Val  Asn  Ile  Ile  Ser  Leu  His  Ile  Trp
          320                      325                      330

GAA  CTC  AGC  TCC  ATC  AAG  AAT  TCC  TTA  AAG  GTT  GCT  GCT  ATC  TCT  GAG       1056
Glu  Leu  Ser  Ser  Ile  Lys  Asn  Ser  Leu  Lys  Val  Ala  Ala  Ile  Ser  Glu
     335                      340                      345

TCA  CCG  GCT  GCA  GAG  AAG  GAG  AAT  CAG  CAA  GCA  TCT  AGT  GAG  GCT  GGA       1104
Ser  Pro  Ala  Ala  Glu  Lys  Glu  Asn  Gln  Gln  Ala  Ser  Ser  Glu  Ala  Gly
350                      355                      360                      365

CTG  TAAGTCAATG  CA                                                                  1119
Leu
```

( 2 ) INFORMATION FOR SEQ ID NO:2:

( i ) SEQUENCE CHARACTERISTICS:
        ( A ) LENGTH: 369 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Ser  Thr  Thr  Met  Ser  Ile  Asn  Ser  Ser  Lys  Gln  Pro  Ala  Ser  Ser  Ala
-3             1                   5                        10

Ala  Gly  Leu  Ile  Ala  Asn  Thr  Thr  Cys  Gln  Thr  Glu  Asn  Arg  Leu  Ser
          15                  20                       25

Val  Phe  Phe  Ser  Ile  Ile  Phe  Met  Thr  Val  Gly  Ile  Val  Ser  Asn  Ser
30                       35                       40                       45

Leu  Ala  Ile  Ala  Ile  Leu  Met  Lys  Ala  Tyr  Gln  Arg  Phe  Arg  Arg  Lys
                    50                       55                            60

Ser  Lys  Ala  Ser  Phe  Leu  Leu  Leu  Ala  Ser  Gly  Leu  Val  Ile  Thr  Asp
               65                       70                       75

Phe  Phe  Gly  His  Leu  Ile  Asn  Gly  Gly  Ile  Ala  Val  Phe  Val  Tyr  Ala
          80                       85                       90

Ser  Asp  Lys  Asp  Trp  Ile  Arg  Phe  Asp  Gln  Ser  Asn  Ile  Leu  Cys  Ser
     95                      100                     105

Val  Phe  Gly  Ile  Ser  Met  Val  Phe  Ser  Gly  Leu  Cys  Pro  Leu  Phe  Leu
110                      115                     120                     125

Gly  Ser  Thr  Met  Ala  Ile  Glu  Arg  Cys  Ile  Gly  Val  Thr  Asn  Pro  Leu
               130                          135                     140

Phe  His  Ser  Thr  Lys  Ile  Thr  Ser  Lys  His  Val  Lys  Met  Ile  Leu  Ser
               145                     150                     155

Gly  Val  Cys  Met  Phe  Ala  Val  Phe  Val  Ala  Leu  Leu  Pro  Ile  Leu  Gly
          160                     165                     170

His  Arg  Asp  Tyr  Gln  Ile  Gln  Ala  Ser  Arg  Thr  Trp  Cys  Phe  Tyr  Asn
     175                     180                     185

Thr  Glu  His  Ile  Glu  Asp  Trp  Glu  Asp  Arg  Phe  Tyr  Leu  Leu  Phe  Phe
190                      195                     200                     205
```

```
Ser  Ser  Leu  Gly  Leu  Leu  Ala  Leu  Gly  Ile  Ser  Phe  Ser  Cys  Asn  Ala
               210                 215                           220

Val  Thr  Gly  Val  Thr  Leu  Leu  Arg  Val  Lys  Phe  Arg  Ser  Gln  Gln  His
               225                 230                           235

Arg  Gln  Gly  Arg  Ser  His  His  Leu  Glu  Met  Val  Ile  Gln  Leu  Leu  Ala
          240                      245                      250

Ile  Met  Cys  Val  Ser  Cys  Val  Cys  Trp  Ser  Pro  Phe  Leu  Val  Thr  Met
     255                      260                      265

Ala  Asn  Ile  Ala  Ile  Asn  Gly  Asn  Asn  Ser  Pro  Val  Thr  Cys  Glu  Thr
270                      275                      280                      285

Thr  Leu  Phe  Ala  Leu  Arg  Met  Ala  Thr  Trp  Asn  Gln  Ile  Leu  Asp  Pro
                    290                      295                      300

Trp  Val  Tyr  Ile  Leu  Leu  Arg  Lys  Ala  Val  Leu  Arg  Asn  Leu  Tyr  Lys
               305                      310                      315

Leu  Ala  Ser  Arg  Cys  Cys  Gly  Val  Asn  Ile  Ile  Ser  Leu  His  Ile  Trp
          320                      325                      330

Glu  Leu  Ser  Ser  Ile  Lys  Asn  Ser  Leu  Lys  Val  Ala  Ala  Ile  Ser  Glu
     335                      340                      345

Ser  Pro  Ala  Ala  Glu  Lys  Glu  Asn  Gln  Gln  Ala  Ser  Ser  Glu  Ala  Gly
350                      355                      360                      365

Leu
```

( 2 ) INFORMATION FOR SEQ ID NO:3:

( i ) SEQUENCE CHARACTERISTICS:
( A ) LENGTH: 385 amino acids
( B ) TYPE: amino acid
( C ) STRANDEDNESS: Not Relevant
( D ) TOPOLOGY: linear ( i i ) MOLECULE TYPE: peptide ( x i ) SEQUENCE DESCRIPTION: SEQ ID NO:3:

```
Met  Ala  Ser  Met  Trp  Ala  Pro  Glu  His  Ser  Ala  Glu  Xaa  Ala  His  Ser
1              5                        10                       15

Asn  Leu  Ser  Ser  Thr  Thr  Asp  Asp  Cys  Gly  Ser  Val  Xaa  Ser  Val  Ala
               20                      25                       30

Phe  Pro  Ile  Thr  Met  Met  Val  Thr  Gly  Phe  Val  Gly  Asn  Ala  Leu  Ala
               35                      40                       45

Met  Leu  Leu  Val  Ser  Arg  Ser  Tyr  Arg  Arg  Arg  Glu  Ser  Lys  Arg  Lys
     50                      55                       60

Lys  Ser  Phe  Leu  Leu  Cys  Ile  Gly  Trp  Leu  Ala  Leu  Thr  Asp  Leu  Val
65                       70                       75                       80

Gly  Gln  Leu  Leu  Thr  Ser  Pro  Val  Val  Ile  Leu  Val  Tyr  Leu  Ser  Gln
               85                      90                       95

Arg  Arg  Trp  Glu  Gln  Leu  Asp  Pro  Ser  Gly  Arg  Leu  Cys  Thr  Phe  Phe
               100                     105                      110

Gly  Leu  Thr  Met  Thr  Val  Phe  Gly  Leu  Ser  Ser  Leu  Leu  Val  Ala  Ser
          115                     120                      125

Ala  Met  Ala  Val  Glu  Arg  Ala  Leu  Ala  Ile  Arg  Ala  Pro  His  Trp  Xaa
          130                     135                      140

Xaa  Xaa  Tyr  Ala  Ser  His  Met  Lys  Thr  Arg  Ala  Thr  Pro  Val  Leu  Leu
145                     150                      155                      160

Gly  Val  Trp  Leu  Ser  Val  Leu  Ala  Phe  Ala  Leu  Leu  Pro  Val  Leu  Gly
                    165                      170                      175

Val  Gly  Arg  Tyr  Ser  Val  Gln  Trp  Pro  Gly  Thr  Trp  Cys  Phe  Ile  Ser
               180                      185                      190
```

```
Thr Gly Pro Ala Gly Asn Glu Thr Asp Pro Ala Arg Glu Pro Gly Ser
    195                 200                 205
Val Ala Phe Ala Ser Ala Phe Ala Cys Leu Gly Leu Leu Ala Leu Val
    210                 215                 220
Val Thr Phe Ala Cys Asn Leu Ala Thr Ile Lys Ala Leu Val Ser Arg
225                 230                 235                 240
Xaa Cys Arg Ala Lys Ala Ala Val Ser Gln Ser Ser Ala Gln Trp Gly
            245                 250                 255
Arg Ile Thr Thr Glu Thr Ala Ile Gln Leu Met Gly Ile Met Cys Val
            260                 265                 270
Leu Ser Val Cys Trp Ser Pro Leu Leu Ile Met Met Leu Lys Met Ile
        275                 280                 285
Phe Asn Gln Met Ser Val Glu Gln Cys Lys Thr Gln Met Gly Lys Glu
    290                 295                 300
Lys Glu Cys Asn Ser Phe Leu Ile Ala Val Arg Leu Ala Ser Leu Asn
305                 310                 315                 320
Gln Ile Leu Asp Pro Trp Val Tyr Leu Leu Leu Arg Lys Ile Leu Leu
            325                 330                 335
Arg Lys Phe Cys Xaa Xaa Xaa Xaa Xaa Xaa Xaa Xaa Xaa Xaa Xaa Xaa
            340                 345                 350
Xaa Xaa Gln Ile Arg Asp His Thr Asn Tyr Ala Ser Ser Ser Thr Ser
        355                 360                 365
Leu Pro Cys Pro Gly Ser Ser Ala Leu Met Trp Ser Asp Gln Leu Glu
    370                 375                 380
Arg

385
```

( 2 ) INFORMATION FOR SEQ ID NO:4:

( i ) SEQUENCE CHARACTERISTICS:
        ( A ) LENGTH: 378 amino acids
        ( B ) TYPE: amino acid
        ( C ) STRANDEDNESS: Not Relevant
        ( D ) TOPOLOGY: linear ( i i ) MOLECULE TYPE: peptide ( x i ) SEQUENCE DESCRIPTION: SEQ ID NO:4:

```
Xaa Met Trp Pro Asn Gly Ser Xaa Xaa Ser Leu Gly Pro Cys Phe Arg
1               5                   10                  15
Pro Thr Asn Ile Thr Leu Glu Glu Arg Arg Leu Ile Ala Ser Pro Trp
            20                  25                  30
Phe Ala Ala Ser Phe Cys Val Val Gly Leu Ala Ser Asn Leu Leu Ala
        35                  40                  45
Leu Ser Val Leu Ala Xaa Gly Ala Arg Gln Gly Gly Ser His Thr Arg
        50                  55                  60
Ser Ser Phe Leu Thr Phe Leu Cys Gly Leu Val Leu Thr Asp Phe Leu
65                  70                  75                  80
Gly Leu Leu Val Thr Gly Thr Ile Val Val Ser Gln His Ala Ala Leu
            85                  90                  95
Phe Glu Trp His Ala Val Asp Pro Gly Cys Arg Leu Cys Arg Phe Met
            100                 105                 110
Gly Val Val Met Ile Phe Phe Gly Leu Ser Pro Leu Leu Leu Gly Ala
        115                 120                 125
Ala Met Ala Ser Glu Arg Tyr Leu Gly Ile Thr Arg Pro Phe Ser Arg
        130                 135                 140
```

| | | | | | | | | | | | | | | | |
|---|---|---|---|---|---|---|---|---|---|---|---|---|---|---|---|
| Pro | Ala | Val | Ala | Ser | Gln | Arg | Arg | Ala | Trp | Ala | Thr | Val | Gly | Leu | Xaa |
| 145 | | | | | 150 | | | | | 155 | | | | | 160 |
| Xaa | Val | Trp | Ala | Ala | Ala | Leu | Ala | Leu | Gly | Leu | Leu | Pro | Leu | Leu | Gly |
| | | | | 165 | | | | | 170 | | | | | 175 | |
| Val | Gly | Arg | Tyr | Thr | Val | Gln | Tyr | Pro | Gly | Ser | Trp | Cys | Phe | Leu | Thr |
| | | | 180 | | | | | 185 | | | | | 190 | | |
| Leu | Gly | Ala | Xaa | Xaa | Xaa | Xaa | Xaa | Xaa | Xaa | Xaa | Xaa | Glu | Ser | Gly | Asp |
| | | 195 | | | | | 200 | | | | | 205 | | | |
| Val | Ala | Phe | Gly | Leu | Leu | Phe | Ser | Met | Leu | Gly | Gly | Leu | Ser | Val | Gly |
| | 210 | | | | | 215 | | | | | 220 | | | | |
| Leu | Ser | Phe | Leu | Leu | Asn | Thr | Val | Ser | Val | Ala | Thr | Leu | Cys | His | Val |
| 225 | | | | | 230 | | | | | 235 | | | | | 240 |
| Xaa | Tyr | His | Gly | Gln | Glu | Ala | Ala | Gln | Gln | Arg | Pro | Arg | Asp | Ser | Glu |
| | | | | 245 | | | | | 250 | | | | | 255 | |
| Xaa | Xaa | Xaa | Val | Glu | Met | Met | Ala | Gln | Leu | Leu | Gly | Ile | Met | Val | Val |
| | | | 260 | | | | | 265 | | | | | 270 | | |
| Ala | Ser | Val | Cys | Trp | Leu | Pro | Leu | Leu | Val | Phe | Ile | Ala | Gln | Thr | Val |
| | | 275 | | | | | 280 | | | | | 285 | | | |
| Leu | Arg | Asn | Pro | Pro | Ala | Met | Ser | Pro | Ala | Gly | Gln | Leu | Ser | Arg | Thr |
| | 290 | | | | | 295 | | | | | 300 | | | | |
| Thr | Glu | Xaa | Lys | Glu | Leu | Ile | Tyr | Leu | Arg | Val | Ala | Thr | Trp | Asn |
| 305 | | | | | 310 | | | | | 315 | | | | | 320 |
| Gln | Ile | Leu | Asp | Pro | Trp | Val | Tyr | Ile | Leu | Phe | Arg | Arg | Ala | Val | Leu |
| | | | | 325 | | | | | 330 | | | | | 335 | |
| Arg | Arg | Leu | Xaa | Xaa | Xaa | Xaa | Xaa | Xaa | Xaa | Xaa | Xaa | Xaa | Xaa | Xaa |
| | | | 340 | | | | | 345 | | | | | 350 | | |
| Xaa | Xaa | Gln | Pro | Arg | Leu | Ser | Thr | Arg | Pro | Arg | Ser | Leu | Ser | Leu | Gln |
| | | 355 | | | | | 360 | | | | | 365 | | | |
| Pro | Gln | Leu | Thr | Gln | Arg | Ser | Gly | Leu | Gln |
| | 370 | | | | | 375 | | | |

(2) INFORMATION FOR SEQ ID NO:5:

(i) SEQUENCE CHARACTERISTICS:
      (A) LENGTH: 390 amino acids
      (B) TYPE: amino acid
      (C) STRANDEDNESS: Not Relevant
      (D) TOPOLOGY: linear (ii) MOLECULE TYPE: peptide (xi) SEQUENCE DESCRIPTION: SEQ ID NO:5:

| | | | | | | | | | | | | | | | |
|---|---|---|---|---|---|---|---|---|---|---|---|---|---|---|---|
| Xaa | Met | Ser | Ile | Asn | Ser | Ser | Lys | Gln | Pro | Ala | Ser | Ser | Ala | Ala | Gly |
| 1 | | | | 5 | | | | | 10 | | | | | 15 | |
| Leu | Ile | Ala | Asn | Thr | Thr | Cys | Gln | Thr | Glu | Asn | Arg | Leu | Ser | Val | Phe |
| | | | | 20 | | | | | 25 | | | | | 30 | |
| Phe | Ser | Ile | Ile | Phe | Met | Thr | Val | Gly | Ile | Val | Ser | Asn | Ser | Leu | Ala |
| | | | 35 | | | | | 40 | | | | | 45 | | |
| Ile | Ala | Ile | Leu | Met | Lys | Ala | Tyr | Gln | Arg | Phe | Arg | Arg | Lys | Ser | Lys |
| | 50 | | | | | 55 | | | | | 60 | | | | |
| Ala | Ser | Phe | Leu | Leu | Leu | Ala | Ser | Gly | Leu | Val | Ile | Thr | Asp | Phe | Phe |
| 65 | | | | | 70 | | | | | 75 | | | | | 80 |
| Gly | His | Leu | Ile | Asn | Gly | Gly | Ile | Ala | Val | Phe | Val | Tyr | Ala | Ser | Asp |
| | | | | 85 | | | | | 90 | | | | | 95 | |
| Lys | Asp | Trp | Ile | Arg | Phe | Asp | Gln | Ser | Asn | Ile | Leu | Cys | Ser | Val | Phe |
| | | | 100 | | | | | 105 | | | | | 110 | | |

Gly Ile Ser Met Val Phe Ser Gly Leu Cys Pro Leu Phe Leu Gly Ser
         115                 120                 125
Thr Met Ala Ile Glu Arg Cys Ile Gly Val Thr Asn Pro Leu Phe His
    130                 135                 140
Ser Thr Lys Ile Thr Ser Lys His Val Lys Xaa Xaa Met Ile Leu Ser
145                 150                 155                     160
Gly Val Cys Met Phe Ala Val Phe Val Ala Leu Leu Pro Ile Leu Gly
                165                 170                 175
His Arg Asp Tyr Gln Ile Gln Ala Ser Arg Thr Trp Cys Phe Tyr Asn
            180             185                 190
Thr Glu His Ile Glu Xaa Xaa Xaa Xaa Xaa Xaa Asp Trp Glu Asp
        195             200                 205
Arg Phe Tyr Leu Leu Phe Phe Ser Ser Leu Gly Leu Leu Ala Leu Gly
    210                 215                 220
Ile Ser Phe Ser Cys Asn Ala Val Thr Gly Val Thr Leu Leu Arg Val
225                 230                 235                     240
Lys Phe Arg Ser Gln Gln His Arg Gln Gly Arg Ser His His Xaa Xaa
                245                 250                 255
Xaa Xaa Xaa Leu Glu Met Val Ile Gln Leu Leu Ala Ile Met Cys Val
            260                 265                 270
Ser Cys Val Cys Trp Ser Pro Phe Leu Val Thr Met Ala Asn Ile Ala
        275                 280                 285
Ile Asn Gly Asn Xaa Xaa Xaa Xaa Xaa Xaa Xaa Asn Ser Pro Val
    290                 295                 300
Thr Xaa Cys Glu Thr Thr Leu Phe Ala Leu Arg Met Ala Thr Trp Asn
305                 310                 315                     320
Gln Ile Leu Asp Pro Trp Val Tyr Ile Leu Leu Arg Lys Ala Val Leu
                325                 330                 335
Arg Asn Leu Tyr Lys Leu Ala Ser Arg Cys Cys Gly Val Asn Ile Ile
            340                 345                 350
Ser Leu His Ile Trp Glu Leu Ser Ser Ile Lys Asn Ser Leu Lys Val
        355                 360                 365
Ala Ala Ile Ser Glu Ser Pro Ala Ala Glu Lys Glu Asn Gln Gln Ala
    370                 375                 380
Ser Ser Glu Ala Gly Leu
385                 390

(2) INFORMATION FOR SEQ ID NO:6:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: modified_base
        (B) LOCATION: 3
        (D) OTHER INFORMATION: /mod_base=i (ix) FEATURE:
        (A) NAME/KEY: modified_base
        (B) LOCATION: 4
        (D) OTHER INFORMATION: /mod_base=i (ix) FEATURE:
        (A) NAME/KEY: modified_base
        (B) LOCATION: 8
        (D) OTHER INFORMATION: /mod_base=i ( i x ) FEATURE:
    ( A ) NAME/KEY: modified_base
    ( B ) LOCATION: 15
    ( D ) OTHER INFORMATION: /mod_base=i ( i x ) FEATURE:
    ( A ) NAME/KEY: modified_base
    ( B ) LOCATION: 16
    ( D ) OTHER INFORMATION: /mod_base=i ( i x ) FEATURE:
    ( A ) NAME/KEY: modified_base
    ( B ) LOCATION: 18
    ( D ) OTHER INFORMATION: /mod_base=i ( i x ) FEATURE:
    ( A ) NAME/KEY: modified_base
    ( B ) LOCATION: 19
    ( D ) OTHER INFORMATION: /mod_base=i ( x i ) SEQUENCE DESCRIPTION: SEQ ID NO:6:

ATNN Y SWN Y Y TGGCNNTNNC- 24
CGAT ( 2 ) INFORMATION FOR SEQ ID NO:7:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: modified_base
        ( B ) LOCATION: 6
        ( D ) OTHER INFORMATION: /mod_base=i ( i x ) FEATURE:
        ( A ) NAME/KEY: modified_base
        ( B ) LOCATION: 9
        ( D ) OTHER INFORMATION: /mod_base=i ( i x ) FEATURE:
        ( A ) NAME/KEY: modified_base
        ( B ) LOCATION: 15
        ( D ) OTHER INFORMATION: /mod_base=i ( i x ) FEATURE:
        ( A ) NAME/KEY: modified_base
        ( B ) LOCATION: 21
        ( D ) OTHER INFORMATION: /mod_base=i ( x i ) SEQUENCE DESCRIPTION: SEQ ID NO:7:

CKRAANAGNA TRTANACCCA NGGGTC 26

( 2 ) INFORMATION FOR SEQ ID NO:8:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:8:

CCAGCTTCTG GGTATAATGT GTGT 24

( 2 ) INFORMATION FOR SEQ ID NO:9:

( i ) SEQUENCE CHARACTERISTICS:
        ( A ) LENGTH: 50 base pairs ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:9:

AGCAGSATAT ARGCCCAGGG GTCCAAGATC TGGTTCCRGG WTGCCATKCG     50